United States Patent
Freissmuth et al.

(10) Patent No.: US 10,086,001 B2
(45) Date of Patent: *Oct. 2, 2018

(54) COMPOSITION FOR THE TREATMENT OF CYSTIC FIBROSIS

(71) Applicant: SciPharm SàRL, Junglinster (LU)

(72) Inventors: Michael Freissmuth, Vienna (AT); Xaver Koenig, Moedling (AT); Christina Just, Vienna (AT)

(73) Assignee: SciPharm SaRL, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,914

(22) Filed: Dec. 22, 2015

(65) Prior Publication Data

US 2016/0175319 A1    Jun. 23, 2016

Related U.S. Application Data

(63) Continuation of application No. 13/389,281, filed as application No. PCT/EP2010/061428 on Aug. 5, 2010, now abandoned.

(30) Foreign Application Priority Data

Aug. 7, 2009    (EP) .................................. 09167491

(51) Int. Cl.
 *A61K 31/5575* (2006.01)
 *A61K 9/00* (2006.01)
 *A61K 31/5578* (2006.01)
 *A61K 31/5585* (2006.01)

(52) U.S. Cl.
 CPC .......... *A61K 31/5575* (2013.01); *A61K 9/007* (2013.01); *A61K 9/0019* (2013.01); *A61K 9/0053* (2013.01); *A61K 31/5578* (2013.01); *A61K 31/5585* (2013.01)

(58) Field of Classification Search
 CPC ............ A61K 31/5578; A61K 31/5585; A61K 31/5575; A61K 9/0053; A61K 9/007; A61K 9/0019
 See application file for complete search history.

(56) References Cited

U.S. PATENT DOCUMENTS

2003/0130352 A1\* 7/2003 Ueno .................... C07C 405/00
                                                                 514/573
2004/0105819 A1\* 6/2004 Hale ...................... A61K 9/007
                                                                 424/45

FOREIGN PATENT DOCUMENTS

WO      2005/007081         1/2005
WO      WO 2008098196 A1 \*  8/2008 ........... A61K 31/557

OTHER PUBLICATIONS

Tissieres et al (2004). "Aerolized Iloprost as a Bridge to Lung Transplantation in a Patient with Cystic Fibrosis and Pulmonary Hypertension". Ann Thorac Surg., 17: e48-50.\*
Remodulin: About Remodulin [Retrieved from the Internet Aug. 14, 2015], URL: http://web.archive.org/web/20051026083741/http://www.remodulin.com/about.asp.

\* cited by examiner

*Primary Examiner* — Doan T Phan
(74) *Attorney, Agent, or Firm* — Loza & Loza, LLP; Michael Fedrick

(57) ABSTRACT

The present invention provides compositions comprising a prostacyclin or prostacyclin analog, or a pharmaceutically acceptable salt thereof for use in preventing or treating cystic fibrosis. The invention also provides the use of a kit comprising a prostacyclin or prostacyclin analog for treating or preventing a condition associated with cystic fibrosis in a subject.

7 Claims, 2 Drawing Sheets

COMPOSITION FOR THE TREATMENT OF CYSTIC FIBROSIS

CROSS-REFERENCE TO RELATED APPLICATIONS

Figure 1:
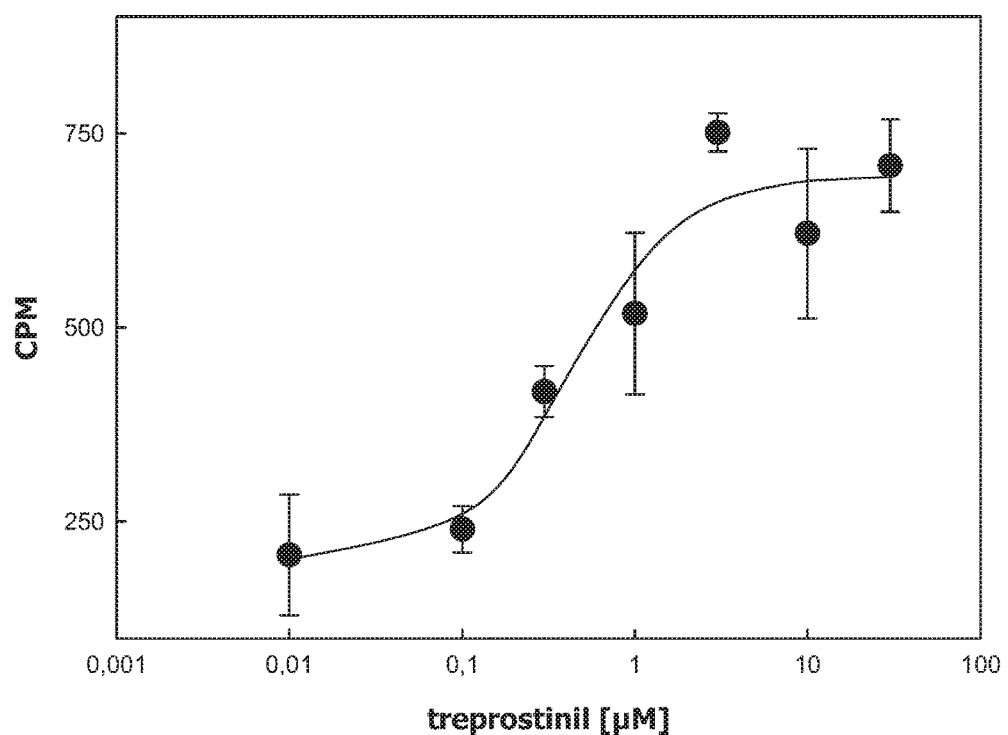

This application is a continuation of U.S. patent application Ser. No. 13/389,281, filed on Feb. 7, 2012 and entitled COMPOSITION FOR THE TREATMENT OF CYSTIC FIBROSIS, which is the U.S. national stage of International Patent Application No. PCT/EP2010/061428, filed on Aug. 5, 2010 and entitled COMPOSITION FOR THE TREATMENT OF CYSTIC FIBROSIS, which claims the benefit of priority under 35 U.S.C. § 119 from European Patent Application No. 09167491.1, filed on Aug. 7, 2009. The disclosures of the foregoing applications are incorporated herein by reference in their entirety.

FIELD OF THE INVENTION

The present invention provides compositions comprising a prostacyclin or a prostacyclin analogue or a pharmaceutically acceptable salt thereof for use in preventing or treating cystic fibrosis.

Cystic fibrosis (CF) is a genetic disease resulting from mutations in a 230 kb gene on chromosome 7 encoding a 1480 amino acid polypeptide known as the cystic fibrosis transmembrane conductance regulator (CFTR) which serves as a chloride channel in epithelial membranes. Over 1000 mutant alleles have been identified to date. The most common mutation, ΔF508, is the deletion of a phenylalanine residue at codon 508 in the cystic fibrosis transmembrane conductance regulator (CFTR) protein. This mutation results in a severe reduction in CFTR function, and leads to the classic cystic fibrosis phenotype characterized with abnormality in exocrine gland functions like raised sweat chloride, recurrent respiratory infection with bronchiectasis, and early-onset of pancreatic insufficiency.

Clinically, CF is usually suspected when one or more typical CF phenotypic features are present in a subject. This could be a chronic pulmonary disease alone or very often associated with gastrointestinal and nutritional abnormalities (e.g. pancreatic insufficiency and recurrent pancreatitis), salt loss syndromes and male urogenital abnormalities (i.e. obstructive azoospermia). In the human lung, thick, tenacious secretions obstruct the distal airways and submucosal glands, which express CFTR. Ductular dilatation of these glands (associated with blockage by mucus) and the plastering of airway surfaces by thick, viscous, neutrophil dominated mucopurulent debris are among the pathological hallmarks of the disease. Pulmonary inflammation is another major cause of the decline in respiratory function in subjects with cystic fibrosis and may precede the onset of chronic infection. Mucinous impaction and thick concretions within pancreatic ducts lead to chronic fibrosis, fatty replacement of the gland, or both in a large subgroup of subjects with a previous diagnosis of idiopathic or alcoholic pancreatitis.

Cystic fibrosis is the most common fatal inherited disease in the Caucasian population, affecting about 4 in 10,000 children. In the United States, the median age at death has increased from 8.4 years of age in 1969 to 14.3 years of age in 1998. The mean age of death has increased from 14 years in 1969 to 32.4 years of age in 2003 (Cystic Fibrosis Foundation). For children born in the 1990s, the median survival is predicted to be over 40 years. A major contributor to the significant increase in life expectancy is improved treatment of chronic respiratory tract infections and elimination of mucus in CF subjects as well as improved nutrition and earlier diagnosis.

Loss of the cystic fibrosis transmembrane conductance regulator (CFTR) anion conductance from the apical membranes of airway epithelia disrupts regulation of the airway surface liquid layer. This leads to impaired mucociliary clearance, airway infection, and inflammation characteristic of cystic fibrosis (CF). The common ΔF508 mutation of CFTR is present on at least one allele in >90% of CF patients, and >50% of patients are homozygous for ΔF508, the rest being compound heterozygous. A central issue in CF disease is the inability of this common CFTR variant to achieve the native, folded state that will exit from the endoplasmic reticulum (ER) and traffic to the epithelial cell apical membrane.

If acquisition of the native conformation is retarded, CFTR is thought to maintain excessive or prolonged interactions with molecular chaperones, which then target the protein for degradation by mechanisms that police the ER for misfolded or incompletely complexed proteins. ER-associated degradation (ERAD) involves ubiquitination of aberrant proteins and their delivery to the proteasome for digestion. If ERAD lags behind the rate of protein synthesis, or during treatment with proteasome inhibitors, aggregates of the mutant protein accumulate. CFTR was the first integral membrane mammalian protein to be identified as a substrate for ubiquitin-proteasome mediated degradation, and it has served as a model for the growing list of diseases of protein conformation, which account for a diverse set of pathological etiologies.

Essentially all of the ΔF508 CFTR produced by the cell is destroyed by ERAD. Also, due to its complex folding pattern, 60-70% of the wild-type (wt) protein may be similarly degraded, although this may vary among cell types. The proteolytic cleavage patterns of the immature forms of wt and ΔF508 CFTR are similar, whereas the digestion pattern of mature wt CFTR is different. This finding supports the concept that at least a portion of the ER-retained mutant CFTR is present in an intermediate conformation that is formed along the normal CFTR folding pathway, as opposed to the formation of a variant protein structure. For ΔF508 CFTR, this intermediate conformation cannot proceed beyond a critical step in the folding process, but this implies that ΔF508 CFTR could be rescued if it were possible to facilitate this step.

A variety of experimental conditions, such as reduced temperature, incubation with chemical chaperones, or pharmacological correctors, can promote the escape of ΔF508 CFTR from the ER, yielding a functional anion channel at the cell surface. In addition, investigators have reported restoration of ΔF508 CFTR function by coexpression of various partial CFTR constructs or subdomains from wt CFTR. However, a consensus as to which CFTR subdomains are effective in mutant protein rescue is not apparent, and the mechanism of this effect remains obscure. In addition, CFTR fragment-induced rescue has been observed primarily in cells exogenously overexpressing both the CFTR fragment and full-length ΔF508 CFTR.

Prostaglandin I2 (prostacyclin; epoprostenol, PGI2) is an oxygenated metabolite of arachidonic acid formed enzymatically by the sequential activities of cyclooxygenase and PGI synthase enzymes. It is produced constitutively by vascular endothelial and smooth muscle cells and is induced under inflammatory conditions in vascular cells and macrophages.

PGI2 is a potent vasodilator and antithrombotic agent whose effects result from binding to a unique heptahelical G protein-coupled receptor termed the I prostanoid (IP)4 receptor. This receptor is coupled to $G_s$- and activates adenylate cyclase, resulting in an acute burst of intracellular cAMP. Since expression of CFTR and mutated CFTR is dependent on cAMP-dependent, substances which enhance intracellular levels of cAMP are of interest for development of drugs for treatment of CF. Most of these substances, such as forskolin, however, induce a rather unspecific elevation of cAMP, which may have also very harmful effects such as inflammation. Thus there is an unmet need of specific enhancers of cAMP in lung epithelial cells.

Treprostinil is a potent IP receptor agonist, although its specificity for this receptor is unknown. Sprague R. S. et al., 2008, showed that Prostacyclin analogues (UT-15, Remodulin) stimulate receptor-mediated cAMP synthesis and ATP release from rabbit and human erythrocytes.

WO 08/098196 describes the treatment of pulmonary fibrosis using Treprostinil. Pulmonary fibrosis, however, is an interstitial lung disease that is caused by the accumulation of collagen fibres in the lung; this restricts the capacity of the lung to inhale air: the lung loses its compliance and the airway resistance increases (compliance=1/resistance). As the disease progresses there is also an increase in vascular resistance. The site of action of Treprostinil in pulmonary fibrosis is the vasculature and the interstitial space in the alveola.

Tissieres et al. describe studies using iloprost for the treatment of a patient with cystic fibrosis and secondary pulmonary hypertension. It is disclosed that aerolised iloprost was effective in lowering pulmonary artery pressure (The annals of thoracic surgery, vol, 78, no. 3, E48-E50).

US2001/006979 A1 describes the use of prostacyclin derivatives like iloprost or cicaprost for the treatment of fibrotic diseases.

Cystic fibrosis is unrelated to pulmonary fibrosis because it is a disease that originates in the bronchial epithelium. Because of the absence of CFTR, there is too little water in the mucus that covers the bronchial epithelium; accordingly, the cilia cannot move the thick mucus and mucociliary clearance breaks down (mucociliary clearance works like a conveyor belt, where the cilia beat rhythmically in a concentred manner to move the mucus back to the trachea and pharynx, from where it may be cleared by swallowing or coughing etc.). If mucociliary breaks down, the bacteria cannot be removed from the bronchi, the bronchi are colonized by bacteria and there are repeated bouts of lung infections that destroy the lung. The situation can be remedied by restoring Cl-fluxes to the bronchial epithelium. Thus, in cystic fibrosis the site of action is the airway epithelium of the bronchi. The site of action is anatomically distinct (lung interstitium vs. bronchial airway), involves a different set of cells (fibroblasts, vascular smooth muscle cells, endothelium versus absorbing and secreting bronchial epithelial cells) and presumably also involves different receptors (prostacyclin receptor vs possibly EP2-receptor).

Presently, no treatments of cystic fibrosis are available that significantly improve quality of life of patients over a longer period. Therefore it is an object of the invention to provide compositions for treatment that can enhance the expression of ΔF508 CFTR and/or chloride channel function in epithelial cells of the lung.

SHORT DESCRIPTION OF THE INVENTION

The object of the invention is achieved by providing a composition comprising a prostacyclin or an analogue, a derivative or a pharmaceutically acceptable salt thereof for use in preventing or treating cystic fibrosis.

According to a specific embodiment of the invention the prostacyclin analogue is selected from the group of Treprostinil, Iloprost, Cisaprost or Beraprost or pharmaceutically acceptable salts thereof.

More specifically, the Treprostinil derivative can be selected from the group of acid derivatives, prodrugs, sustained release forms, inhaled forms, oral forms, polymorphs or isomers of Treprostinil.

The composition of the invention can be administered by intravenous administration, inhalation or it can be in an orally available form selected from the group of tablets or capsules.

Specifically the composition comprises an effective amount of Treprostinil or its derivative, or a pharmaceutically acceptable salt thereof which is at least 1.0 ng/kg of body weight/min.

Further, according to the present invention the use of a kit for treating or preventing a condition associated with cystic fibrosis in a subject, comprising (i) an effective amount of a prostacyclin or prostacyclin analogue or derivative or a pharmaceutically acceptable salt thereof, specifically a pharmaceutically acceptable salt of Treprostinil, (ii) one or more pharmaceutically acceptable carriers and/or additives, and (iii) instructions for use in treating or preventing cystic fibrosis is provided as well.

FIGURES

FIG. 1: Accumulation of cAMP in IB3-1 cells after incubation with Treprostinil.

Figure 2:
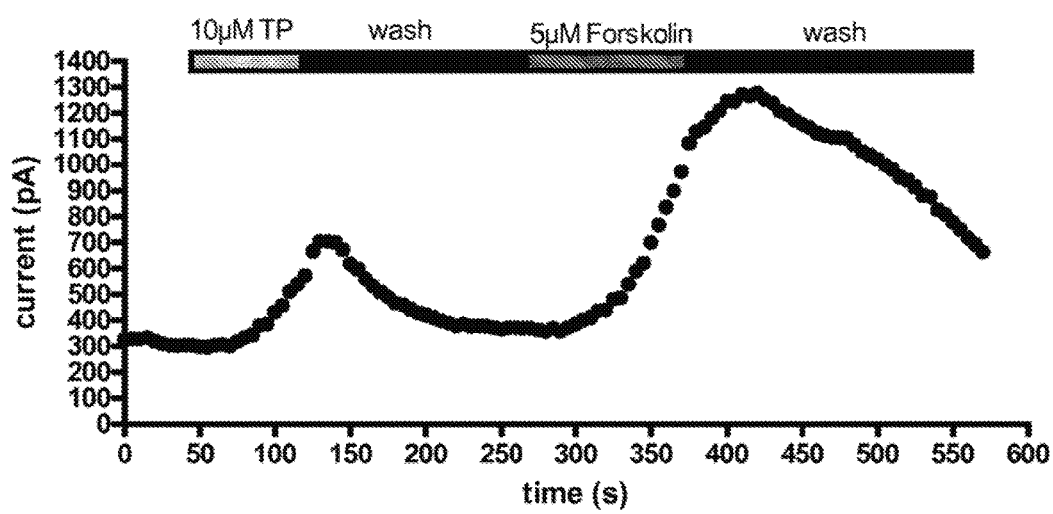

FIG. 2: Activation of a Cl-current by Treprostinil in the human bronchial epithelial IB3-1 cell line transiently expressing CFTR-wt.

DETAILED DESCRIPTION OF THE INVENTION

It has been surprisingly found by the inventors that prostacyclin or analogues or derivatives or a pharmaceutically acceptable salt thereof can be used for treating cystic fibrosis. Synthetic prostacyclin analogues can be for example, but are not limited to Treprostinil, Iloprost, Cisaprost or Beraprost.

Suitable prostacyclin derivatives include but are not limited to acid derivatives, prodrugs, sustained release forms, inhaled forms and oral forms of Treprostinil, Iloprost, Cisaprost or Beraprost.

A pharmaceutically acceptable salt of a prostacyclin or prostacyclin analogue of this invention can be formed between an acid and a basic group of the compound, such as an amino functional group, or a base and an acidic group of the compound, such as a carboxyl functional group. According to another embodiment, the compound is a pharmaceutically acceptable acid addition salt.

Specifically, Treprostinil or its derivative is useful according to the invention. Treprostinil can successfully enhance the expression of ΔF508 CFTR and/or the chloride channel function in epithelial cells of the lung of cystic fibrosis patients.

Specifically, physiologically acceptable salts of Treprostinil include salts derived from bases. Base salts include ammonium salts (such as quaternary ammonium salts), alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

It has been surprisingly shown that a prostacyclin or analogue or derivative thereof leads to stimulation of production of cAMP in bronchoepithelial cells. This mode of action might be via induced activation of the IP receptor. Interestingly the phosphodiesterase inhibitor (PDE3 inhibitor), Anagrelide, did not induce any accumulation cAMP in experiments.

Given this ability to stimulate cAMP production through the IP receptor, and the limited presence of IP receptors to a small number of cell-types (such as epithelial lung cells), a prostacyclin or analogue thereof, for example Treprostinil or a derivative or salt thereof might induce expression and gating of CFTR and mutCFTR in a specific manner can be used for treatment of CF.

The current invention therefore also relates to a composition comprising a prostacyclin or prostacyclin analogue, specifically Treprostinil or its derivative, or a pharmaceutically acceptable salt thereof for use in treating cystic fibrosis as well as therapies of cystic fibrosis using a prostacyclin or prostacyclin analogue, specifically Treprostinil or its derivative, or a pharmaceutically acceptable salt thereof.

Treprostinil is a synthetic analogue of prostacyclin. Treprostinil is marketed as Remodulin™. Treprostinil is a (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid monosodium salt.

According to the invention the derivatives of Treprostinil can be for example acid derivatives of Treprostinil, prodrugs of Treprostinil, sustained release forms of Treprostinil, inhaled forms of Treprostinil, oral forms of Treprostinil, polymorphs of Treprostinil or isomers of Treprostinil.

The composition of the invention can be present in any form which can be used for administration.

The composition of the invention can be administered as liquid or powder. It can be administered topically, intravenously, subcutaneously, by inhalation or by using a nebulizer or in orally available form like tablets or capsules. Due to the high metabolic stability of some prostacyclin analogues like Treprostinil, or if provided as lipid based or pegylated forms of the prostacyclins or prostacyclin analogues, the substances can also be administered as depot medicaments.

Aerosolized delivery of the prostacyclin analogue may result in a more homogeneous distribution of the agent in a lung, so that deep lung delivery is obtained. Thereby the dosage of application might be reduced to the sustained presence of the agent at the site of action in the lung.

The composition can be administered with any pharmaceutically acceptable substances or carriers or excipients as known in the art. These can be for example, but are not restricted to water, neutralizing agents like NaOH, KOH, stabilizers, DMSO, saline, betaine, taurine etc.

The term "pharmaceutically acceptable" means approved by a regulatory agency of the Federal or a state government or listed in the U.S.

The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration.

Treprostinil is of high metabolic stability which specifically allows for administration by various routes.

The amount of the inventive composition can be selected by any skilled person, preferably the amount of the prostacyclins or prostacyclin analogues or pharmaceutically acceptable salts thereof, specifically of Treprostinil is at least 1.0 ng/kg of body weight/min.

The invention further provides a kit for treating or preventing a condition associated with cystic fibrosis in a subject, comprising (i) an effective amount of a prostacyclin or prostacyclin analogue or derivative or a pharmaceutically acceptable salt thereof, (ii) one or more pharmaceutically acceptable carriers and/or additives, and (iii) instructions for use in treating or preventing cystic fibrosis.

According to the embodiment of the invention, the kit comprising (i) an effective amount of a prostacyclin or prostacyclin analogue or a pharmaceutically acceptable salt thereof, (ii) one or more pharmaceutically acceptable carriers and/or additives, and (iii) instructions for use in treating or preventing cystic fibrosis is provided for use in the treatment or prevention of a condition associated with cystic fibrosis in a subject, preferably a human.

Said component (i) can be in a form suitable for intravenous administration, for inhalation or for oral administration. The component (i) can be in a form suitable for intravenous administration, for inhalation or for oral administration.

More specifically, the present invention provides the use of a kit comprising i) an effective amount of Treprostinil or a pharmaceutically acceptable salt thereof, (ii) one or more pharmaceutically acceptable carriers and/or additives, and (iii) instructions for use in treating or preventing cystic fibrosis in the treatment or prevention of a condition associated with cystic fibrosis in a subject, preferably a human.

Specifically, the component (i) is a pharmaceutically acceptable salt of Treprostinil. According to a specific embodiment for the use of the kit, component (i) is in a form suitable for intravenous administration or suitable for inhalation or suitable for oral administration.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

IB3-1 cells were plated on 6 well-plates (0.2*106 cells/well) in complete growth medium (LHC-8+5% FCS). The following day, the adenine nucleotide pool was metabolically labelled by incubation with [3H]adenine (1 µCi/well) in Dulbecco's Modified Eagle Medium (DMEM) containing adenosine deaminase (1 unit/ml) for 4 h. Cyclc AMP formation was stimulated by 20 µM forskolin or the PGI2-analogue treprostinil (Remodulin®). The assay was performed in triplicates. The formation of [$^3$H]cAMP was determined by sequential chromatography on Dowex 50WX-4 and neutral alumina columns followed by liquid scintillation counting of the eluate.

Treprostinil caused a concentration-dependent accumulation of cAMP in IB3-1 cells (FIG. 1). Half-maximum stimulation was seen in the range of 0.3 to 1 µM.

Example 2

IB3-1 cells endogenously express only mutated CFTR-ΔF508, which is retained within the cells. Using appropriated manipulations (e.g., pharmacochaperones or low temperature incubations), it is possible to translocate the mutant CFTR-ΔF508 from the endoplasmic reticulum to the ER; when inserted at the cell surface, a Cl-conductance can be stimulated by elevating cAMP. The resulting Cl-conductance, however, is small. In order to unequivocally prove that the cAMP accumulation induced by Treprostinil translated into an activation of CFTR, we transiently expressed a GFP-tagged version of wild type CFTR (the GFP tag allowed for the identification of cells that expressed the protein at the cell surface). As can be seen from FIG. 2, Treprostinil caused a robust activation of the current induced by a depolarization from −40 mV holding potential to +60 mV. The maximum effect was delayed, i.e. it was only observed several s after wash-in of the compound. Likewise, there was also a hysteresis in the turn-off reaction; the current decayed to basal only ~100 s after washout. These delayed responses reflect the (i) intervening signalling cascade (i.e., the receptor-dependent activation of $G_s$, $G\alpha_s$-dependent activation of cAMP formation and the ensuing protein kinase A-dependent phosphorylation of CFTR) and (ii) the delayed deactivation of increased cAMP by phosphodiesterases. Similar delays were also seen, if cells were stimulated with forskolin, a direct activator a adenylyl cyclase, which was used as a positive control. These observations prove that Treprostinil can activate CFTR in bronchial epithelial cells.

Methods:

Electrophysiology

The whole cell patch clamp technique was used for current recordings performed at 22±1.5° C. using an Axoclamp 200B patch clamp amplifier (Axon Instruments). Pipettes had resistances between 1 and 2 MΩ when filled with the recording pipette solution (composition: 110 mM CsCl, 5 mM EGTA, 2 mM $MgCl_2$, 1 mM $K_2$.ATP, 10 mM Hepes, pH adjusted to 7.2 with CsOH). Voltage-clamp protocols and data acquisition were performed with pclamp 6.0 software (Axon Instruments). Data were low-pass filtered at 2 kHz (−3 dB) and digitized at 10-20 kHz. Cells were continuously superfused with external solution (composition: 145 mM NaCl, 4.5 mM KCl, 2 mM $CaCl_2$, 1 mM $MgCl_2$, 5 mM glucose, 10 mM Hepes, pH adjusted to 7.4 with NaOH). When indicated, the external solution contained Treprostinil (10 µM) or forskolin (5 µM), switching between solutions was achieved by electronically controlled pressure valves.

Cell Culture:

I3B-1 cells were grown on dishes (Nunc, 3.5 cm diameter) covered with fibronectin (10 µg/mL) rat collagen 1 (30 µg/mL) and BSA 10 µg/mL) in LHC-8 medium (Gibco) containing 5% fetal calf serum (FCS). Cells were transiently transfected with a plasmid driving the expression of human GFP-tagged wild type CFTR by using Lipofectamine Plus® (Invitrogen) according to the instructions of the manufacturer.

Representative current amplitudes recorded in the whole cell patch clamp configuration at +60 mV. A transiently transfected I3B-1 cell expressing GFP-tagged wild type CFTR was selected under fluorescent light and clamped to a holding potential at −40 mV. Depolarization was induced by a voltage step to +60 mV for 50 ms and the current amplitude was recorded. Wash-in of Treprostinil (10 µM final concentration, TP) was initiated at the time point 50 s and terminated at 125 s. Forskolin was washed in at 275 s and was removed at 375 s. Results are shown in FIG. 2.

The invention claimed is:

1. A method of enhancing chloride channel function of cystic fibrosis transmembrane conductance regulator (CFTR) in lung epithelial cells of a subject with cystic fibrosis who expresses the ΔF508 mutation of CFTR, comprising administering to the subject in need thereof an effective amount of treprostinil together with one or more pharmaceutically acceptable carriers and/or additives.

2. The method of claim 1, wherein the treprostinil is in a form suitable for intravenous administration.

3. The method of claim 1, wherein the treprostinil is in a form suitable for inhalation.

4. The method of claim 1, wherein the treprostinil is in a form suitable for oral administration.

5. The method of claim 4, wherein the treprostinil is in a form selected from the group consisting of tablets and capsules.

6. The method of claim 1, wherein the treprostinil is administered in an amount of at least 1.0 ng/kg of the subject's body weight/minute.

7. The method of claim 1, wherein the treprostinil is selected from the group consisting of a sustained release form of treprostinil, an inhaled form of treprostinil, and an oral form of treprostinil.

* * * * *